(12) United States Patent
Hochhalter et al.

(10) Patent No.: US 8,220,628 B2
(45) Date of Patent: Jul. 17, 2012

(54) DEFIBRILLATORS STORAGE AND CARRYING DEVICE

(76) Inventors: Keith W. Hochhalter, Inverness, IL (US); Michael T. Seiler, Kenosha, WI (US)

( * ) Notice: Subject to any disclaimer, the term of this patent is extended or adjusted under 35 U.S.C. 154(b) by 181 days.

(21) Appl. No.: 12/459,960

(22) Filed: Jul. 9, 2009

(65) Prior Publication Data
US 2011/0005953 A1 Jan. 13, 2011

(51) Int. Cl.
*A61B 19/02* (2006.01)
(52) U.S. Cl. ............. 206/363; 607/5; 220/737; 220/481
(58) Field of Classification Search .................. 206/438, 206/776, 569–772, 363, 499; 220/737, 476–483; 607/6, 5
See application file for complete search history.

(56) References Cited

U.S. PATENT DOCUMENTS

| | | | | |
|---|---|---|---|---|
| 3,610,510 A | * | 10/1971 | Lowry | 206/457 |
| 4,955,477 A | * | 9/1990 | Bruno | 206/366 |
| 6,301,501 B1 | | 10/2001 | Cronin et al. | |
| 6,327,497 B1 | * | 12/2001 | Kirchgeorg et al. | 607/3 |
| 6,422,669 B1 | * | 7/2002 | Salvatori et al. | 312/213 |
| 6,735,473 B2 | | 5/2004 | Kolder et al. | |
| 6,758,338 B2 | * | 7/2004 | Lien | 206/534 |
| 7,434,686 B2 | * | 10/2008 | Prindle | 220/478 |

* cited by examiner

*Primary Examiner* — J. Gregory Pickett
*Assistant Examiner* — Andrew Perreault
(74) *Attorney, Agent, or Firm* — Meroni & Meroni, P.C.; Charles F. Meroni, Jr.; Christopher J. Scott

(57) ABSTRACT

A storage assembly houses a defibrillator and enables would-be users to quickly (1) identify the defibrillator location and (2) carry the housed defibrillator to a user site. The storage assembly comprises a cover structure, a mounting assembly, and a defibrillator-restraining assembly. The cover structure comprises an open back, a closed front, a cover wall extending from the front to the back, a heart-shaped transverse cross-section. The cover wall spaces the front from the back and has a transverse periphery thereby defining a space sufficient to receive and house the defibrillator. The mounting assembly removably mounts the cover structure to a support wall, and the defibrillator-restraining assembly removably restrains the defibrillator as received within the cover structure. The cover structure may be nested with at least one additional cover structure for reducing space necessary for storage and the like. An optional alarm may be outfitted with the assembly.

13 Claims, 10 Drawing Sheets

DEFIBRILLATORS STORAGE AND CARRYING DEVICE

BACKGROUND OF THE INVENTION

1. Field of the Invention

The present invention generally relates to a protective defibrillator storage device with an optional alarm system to notify others that a cardiac arrest incident is in progress. More particularly, the present invention relates to a protective defibrillator storage device having both a functional and ornamental visual appearance for enabling would-be users to quickly and visually identify the defibrillator storage vessel of a defibrillator.

2. Description of Prior Art

The prior art relating to defibrillator storage devices is relatively under developed. Typically, defibrillator storage devices and/or assemblies and the like are constructed from sheet metal and visually appear box-like very much akin to the housing for fire extinguishers and/or fire hoses. In other words, the cabinetry or storage housing for defibrillators are often indistinguishable from other emergency hardware, and are not easily identified from a distance. Nevertheless, several attempts have been made to more fully develop defibrillator storage means. Two of the more pertinent prior art disclosures relating to defibrillator storage devices and the like are briefly described hereinafter.

U.S. Pat. No. 5,388,570 ('570 Patent), which issued to Wassil, for example, discloses an Emergency CPR Mask Station. The '570 Patent describes a cabinet housing CPR masks and non-sterile hypoallergenic latex gloves. The cabinet is mounted on a wall in a visible location. A plastic tie seal maintains the cabinet door closed. In the event of a CPR emergency, the seal is pulled, twisted and thereby broken, the door opened and the mask and gloves removed. When the door is opened, a lever switch on the cabinet automatically activates a loud piezo buzzer mounted on top of the cabinet, thereby alerting others to the emergency. The buzzer can be deenergized with a key-activated switch.

U.S. Pat. No. 6,301,501 ('501 Patent), which issued to Cronin et al., discloses a Protective Defibrillator Storage Device with Alarm Signal. The '501 Patent describes a protective defibrillator storage device comprising an enclosure having a plurality of wall sections, a top section, a bottom section and a door section. The wall sections, top section, bottom section, and the door section define an interior compartment. The interior compartment is of sufficient size to house a defibrillator. A defibrillator mount is connected to an interior surface of the enclosure.

Certain alarm means are connected to the enclosure. The alarm means are used to indicate that the door of the protective defibrillator storage device has been opened, and that a cardiac arrest incident is possibly in progress. The alarm means comprise an alarm circuit with a visual alarm signal and an audible alarm signal. Said means are activated when the door section is opened and remains activated until the alarm means are deactivated and reset.

An activation switch triggers the alarm means and is connected to the door section and operatively positioned to contact an enclosure wall when the door is closed. The activation switch is open when the door section is closed, but upon opening of the door section, the activation switch closes activating the alarm means. An alarm deactivating switch is connected to the enclosure and is connected in circuit to the alarm means. The alarm deactivating switch is used to reset the system after the alarm means has been activated or to totally deactivate the alarm means.

U.S. Pat. No. 6,735,473 ('473 Patent), which issued to Kolder et al., discloses a Defibrillator Enclosure with Alarm Signal. The '473 Patent describes a defibrillator storage device comprising an enclosure with wall sections, a top section, a bottom section, and a door section defining an interior compartment of sufficient size to house a defibrillator. A defibrillator mount is connected to the interior of the enclosure.

Certain alarm means having a visual alarm signal and an audible alarm signal are used to indicate that the door of the device has been opened, signaling a possible cardiac arrest incident. An activation switch for triggering the alarm is connected to the door and positioned to contact an enclosure wall when the door is closed. The normally open switch is closed when the door is opened. An alarm deactivating switch connected in circuit to the alarm is used to reset the system or to totally deactivate the alarm.

U.S. Pat. No. 7,020,520 ('520 Patent), which issued to Olson et al., discloses a Defibrillator Enclosure System. The '520 Patent describes a defibrillator enclosure system comprising an automated external defibrillator (AED), an openable cabinet, a detector, and an alarm circuit. The openable cabinet is used to enclose the AED while the detector monitors the presence and absence of the AED within the cabinet. Specifically, upon detecting that the AED is no longer within the cabinet, the detector activates an alarm circuit whereby an alarm indicating the absence of the AED is issued.

The '501 and '473 Patents describe defibrillator storage devices that are generally used for higher traffic public places such as schools, airports, health clubs, and etc. A second type of defibrillator storage device is a portable type carrying case used in police cars, emergency vehicles, aircraft, and etc. A third type of defibrillator storage device or case is used primarily in low traffic areas, where budgets do not permit the cost of a full storage cabinet. This third type of device or "case" typically comprises merely a bracket made of folded sheet metal or heavy gage wire, which bracket functions to temporarily restrain the defibrillator in a ready position until its use is required. Notably, however, the brackets serve only as a low cost means to support the defibrillator on the wall. They offer no protection from damage, dust, or theft and provide no distinctive means of identifying what they are holding from a distance. They also do not typically provide alarms.

Various shortcomings in the prior art are noted. Firstly, full-sized defibrillator-storing cabinetry is typically constructed from sheet metal and thus is expensive both to build and transport. Secondly, state of the art defibrillator-storing cabinetry does not provide readily (and visually) identifiable means for distinguishing the housing unit as containing or storing a defibrillator. In other words, many state of the art defibrillator storage devices appear similar to fire extinguisher storage or fire hose storage cabinets. These types of cabinets are not easily identifiable from a distance.

Thirdly, these cabinets house a defibrillator, as well as support items such as razors, scissors, masks, etc. of which must be gathered and transported to the victim. In addition, with the growing access of these devices for outdoor use, it is desirable to have a convenient means to transport the cabinet contents at the beginning and end of each day. While certain state of the art portable cases provide convenient means for storage and portability, and protect the defibrillator, they are not intended to promote public access of the defibrillators.

The prior art thus perceives a need for a low cost defibrillator storage assembly, which is readily identifiable from afar as housing a defibrillator and which is simple to carry as outfitted with a housed defibrillator to an intended user site.

SUMMARY OF THE INVENTION

It is thus an object of the current invention to provide a low cost, high strength, ultraviolet and corrosion resistant defibrillator storage assembly, which low cost assembly supports lowered cost of transport. It is a further object of the present invention to provide a readily identifiable defibrillator storage assembly so that would-be users may more easily and readily identify its contents in the event of an emergency. It is a further object of the present invention to provide certain convenient means of transport for all storage assembly content in both alarmed and un-alarmed versions.

To achieve the foregoing objectives, the present invention provides a storage assembly for housing a defibrillator that enables would-be users to quickly (1) identify the defibrillator location and (2) carry the housed defibrillator to a user site. The storage assembly comprises a cover structure, a mounting assembly, and a defibrillator-restraining assembly.

The cover structure comprises an open back, a closed front, a cover wall extending from the front to the back, a heart-shaped transverse cross-section. The cover wall spaces the front from the back and has a transverse periphery thereby defining a space sufficient to receive and house the defibrillator.

The mounting assembly removably mounts the cover structure to a support wall, and the defibrillator-restraining assembly removably restrains the defibrillator as received within the cover structure. The cover structure may be nested with at least one additional cover structure for reducing space necessary for storage and the like. An optional alarm may be outfitted with the assembly.

BRIEF DESCRIPTION OF THE DRAWINGS

Other features of our invention will become more evident from a consideration of the following brief description of patent drawings.

DESCRIPTION OF THE PREFERRED EMBODIMENT(s)

Figure 1:
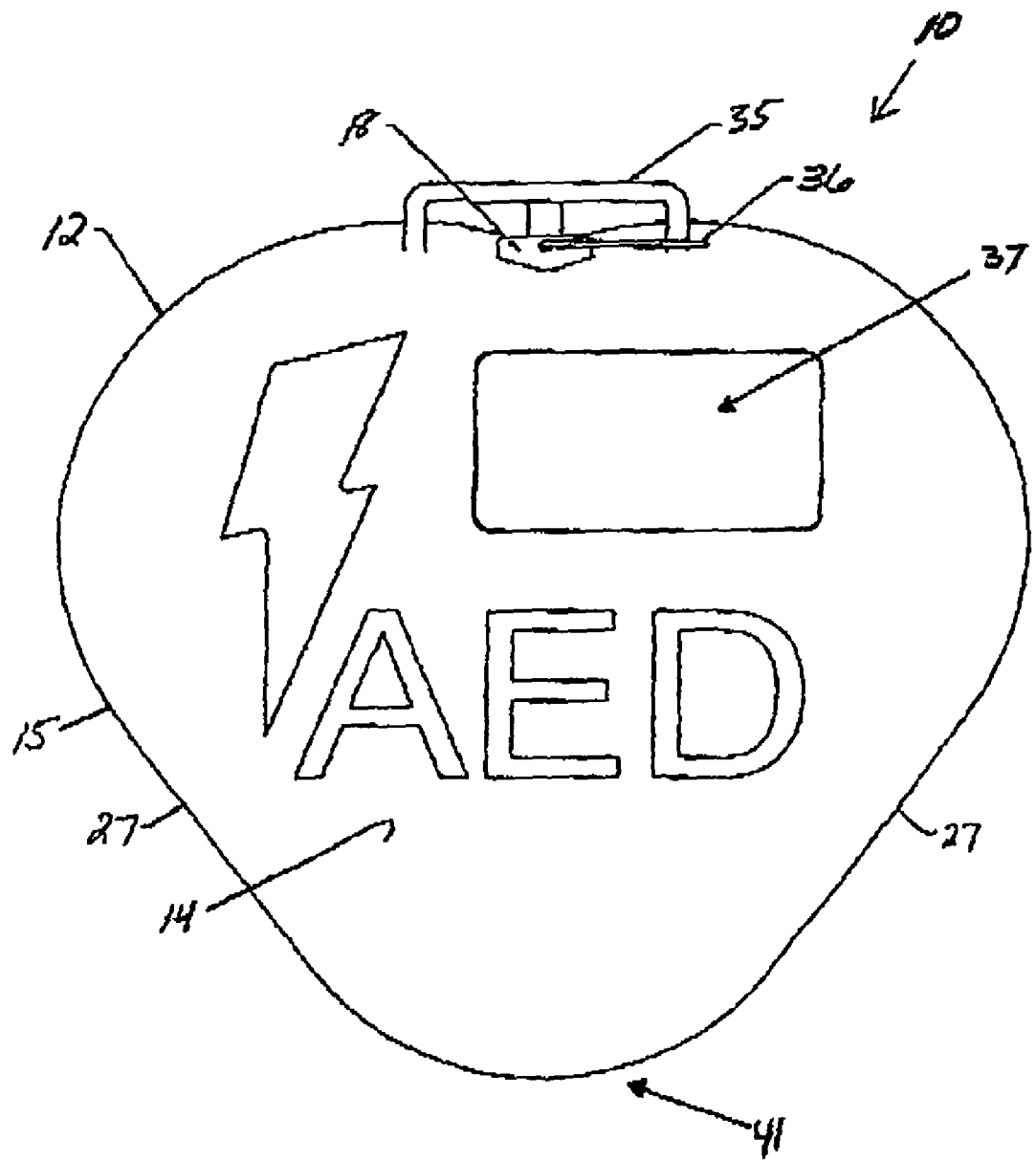
FIG. 1 is an anterior or front plan view of a first defibrillator storage assembly according to the present invention showing a generally heart-shaped form for the outer assembly casing.

Referring now to the drawings with more specificity, the preferred embodiment of the present invention generally concerns a defibrillator-storage device or assembly 10 for use in combination with an automatic external defibrillator 11, which assembly 10 may be used to store or house the AED 11 as well as case-carry the AED 11 to a user site. Thus, the defibrillator storage assembly 10 according to the present invention essentially functions to enable would-be users to quickly identify the location of a defibrillator based upon the visual appearance of the storage casing and to carry the defibrillator or AED 11 to a user site on an as needed basis.

The defibrillator storage assembly 10 preferably comprises a casing or cover structure 12; certain cover mounting means; and certain defibrillator-restraining means. The casing or cover structure 12 preferably comprises an open back 13, a closed front 14, a continuous wall 15 extending from the front 14 to the back 13, and a heart-shaped or ♥-shaped transverse cross-section as may be generally seen from an inspection of FIG. 7.

In other words, the top portion of the casing 12 is preferably dipped as at 40 and the bottom portion of the casing 12 is preferably pointed as at 41 with sloped sides as at 27. The wall 15 is of a sufficient dimension so as to sufficiently space the front 14 from the back 13 (and has a sufficient transverse peripheral dimension) to receive the defibrillator 11 as generally and comparatively depicted in FIGS. 6 and 7.

Figure 2:
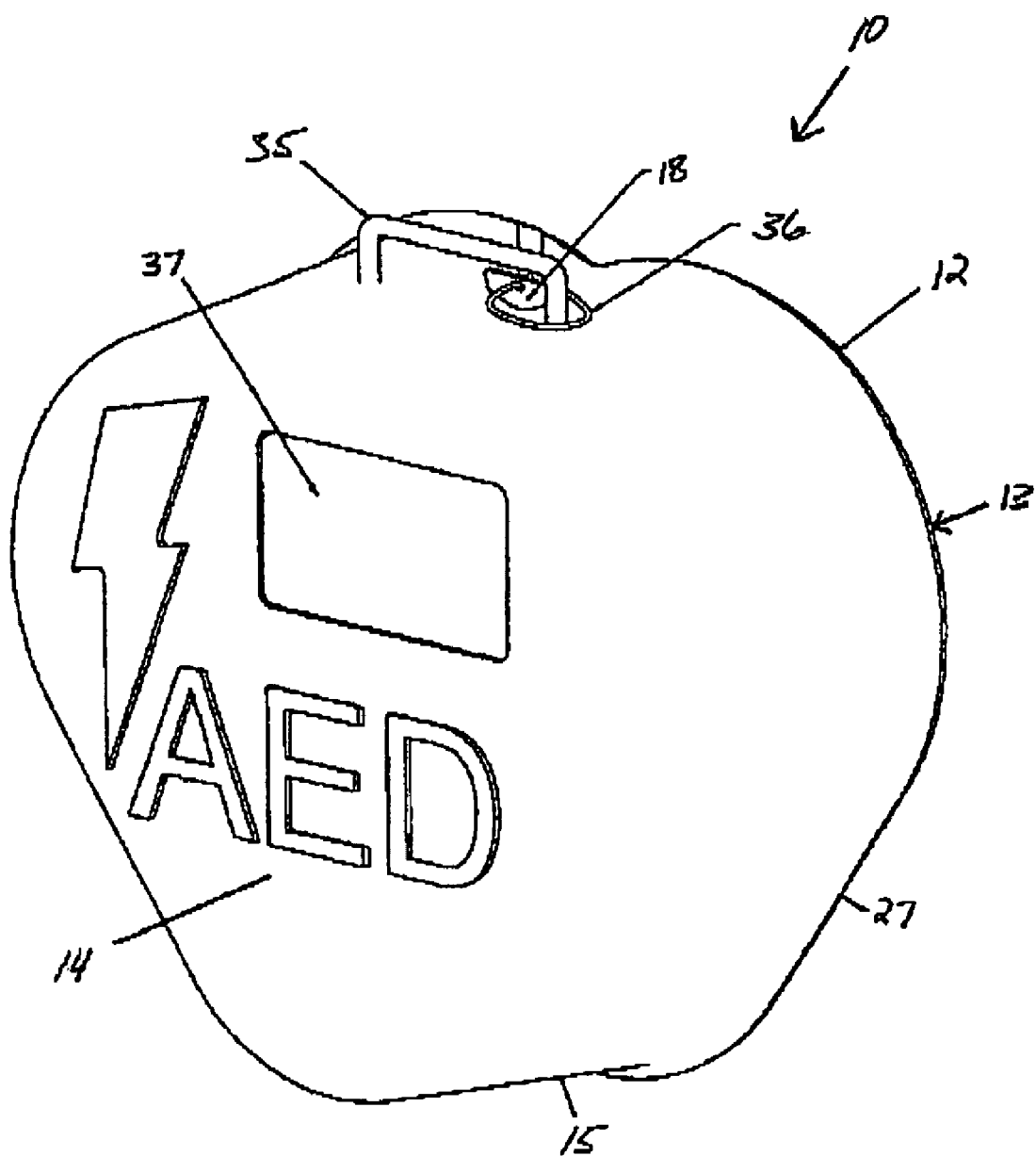
FIG. 2 is top front perspective type view of the defibrillator storage assembly otherwise shown in FIG. 1.

I will be recalled that FIGS. 1 and 2 depict frontal views of a first defibrillator storage assembly 10 according to the present invention showing a generally heart-shaped form for the outer assembly casing 12. The cover-mounting means for assembly 10 is preferably exemplified by a wall bracket 16 as receivable or usable in combination with an aperture or slot 17 formed in an upper portion of the wall 15 of the casing 12.

Figure 7:
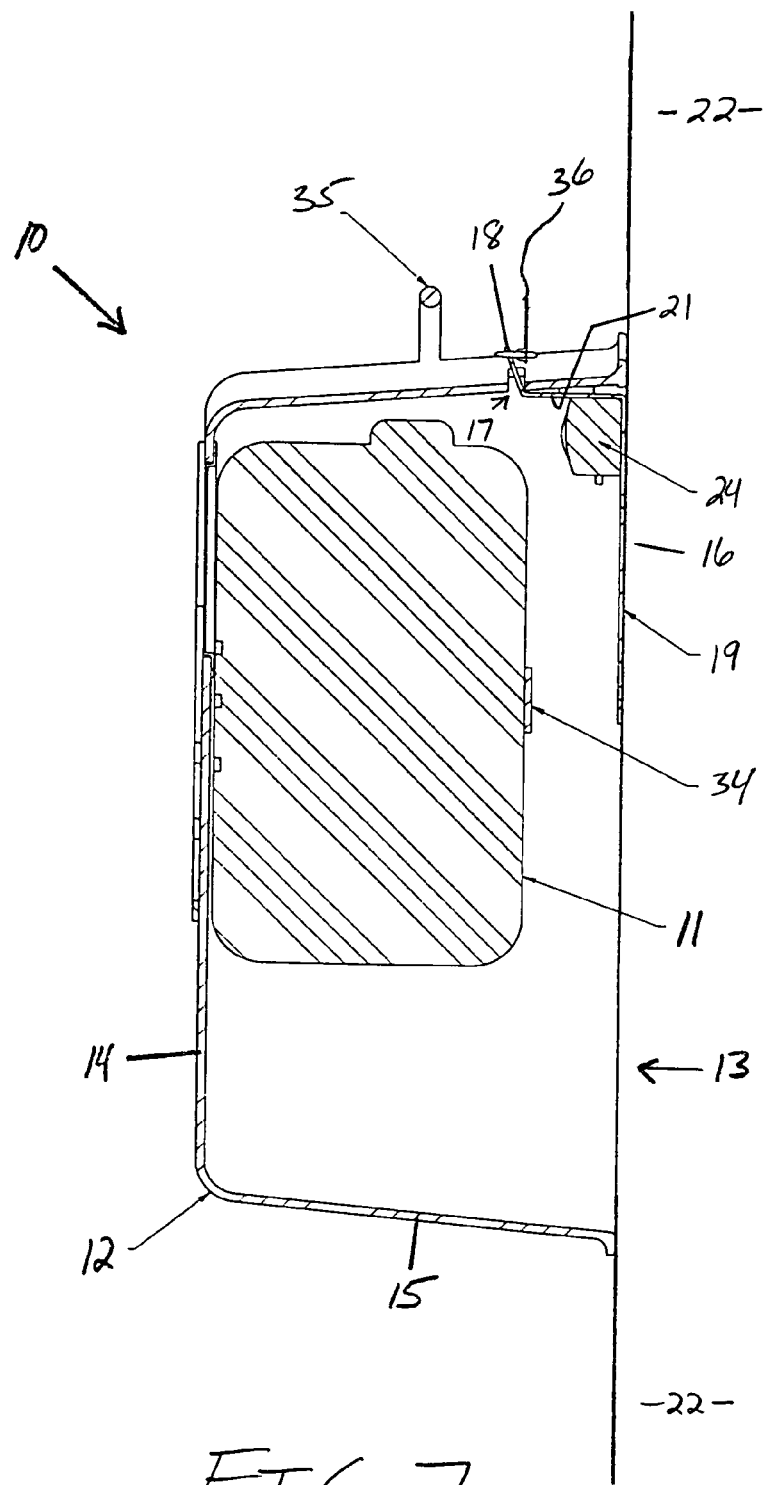
FIG. 7 is a cross-sectional side view of the first defibrillator storage assembly according to the present invention generally showing the wall mounting bracket, the defibrillator restraining strap, the defibrillator restrained by said strap relative to the outer assembly casing.
Figure 8:
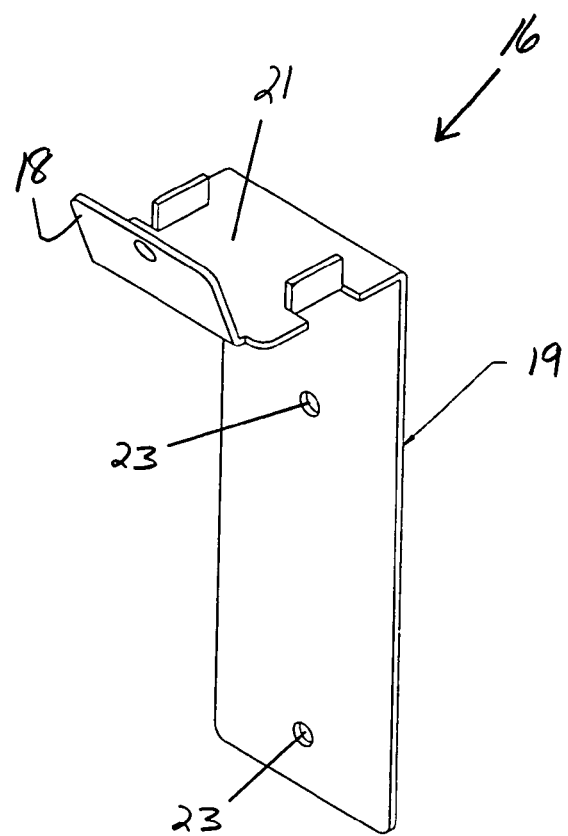
FIG. 8 is a top perspective view of the wall mounting bracket otherwise shown in FIGS. 5 and 6.

The bracket 16 comprises an upper aperture-penetrating or slot-piercing portion 18, a lower wall attachment portion 19, and a casing support portion 21. The portion 19 may thus be fastened to an assembly support wall 22 or similar other support structure by way of fasteners (not specifically shown) receivable through fastener-receiving apertures 23. The slot-piercing portion 18 may then be inserted through slot 17 and the casing 12 may rest upon the casing support portion 21 as further supported by the wall 22 all as generally depicted in FIG. 7.

It is contemplated that lowest cost approach of the present invention is by way of assembly 10, in which case the casing 12 is supported by bracket 16, which bracket 16 is directly attached to wall 22. It is further contemplated that in some situations, customers will want an alarm to sound when the casing 12 is removed from the wall 22/bracket 16. In this event, a first alarm 24 is provided as further illustrated and referenced in FIGS. 6 and 7.

Figure 6:
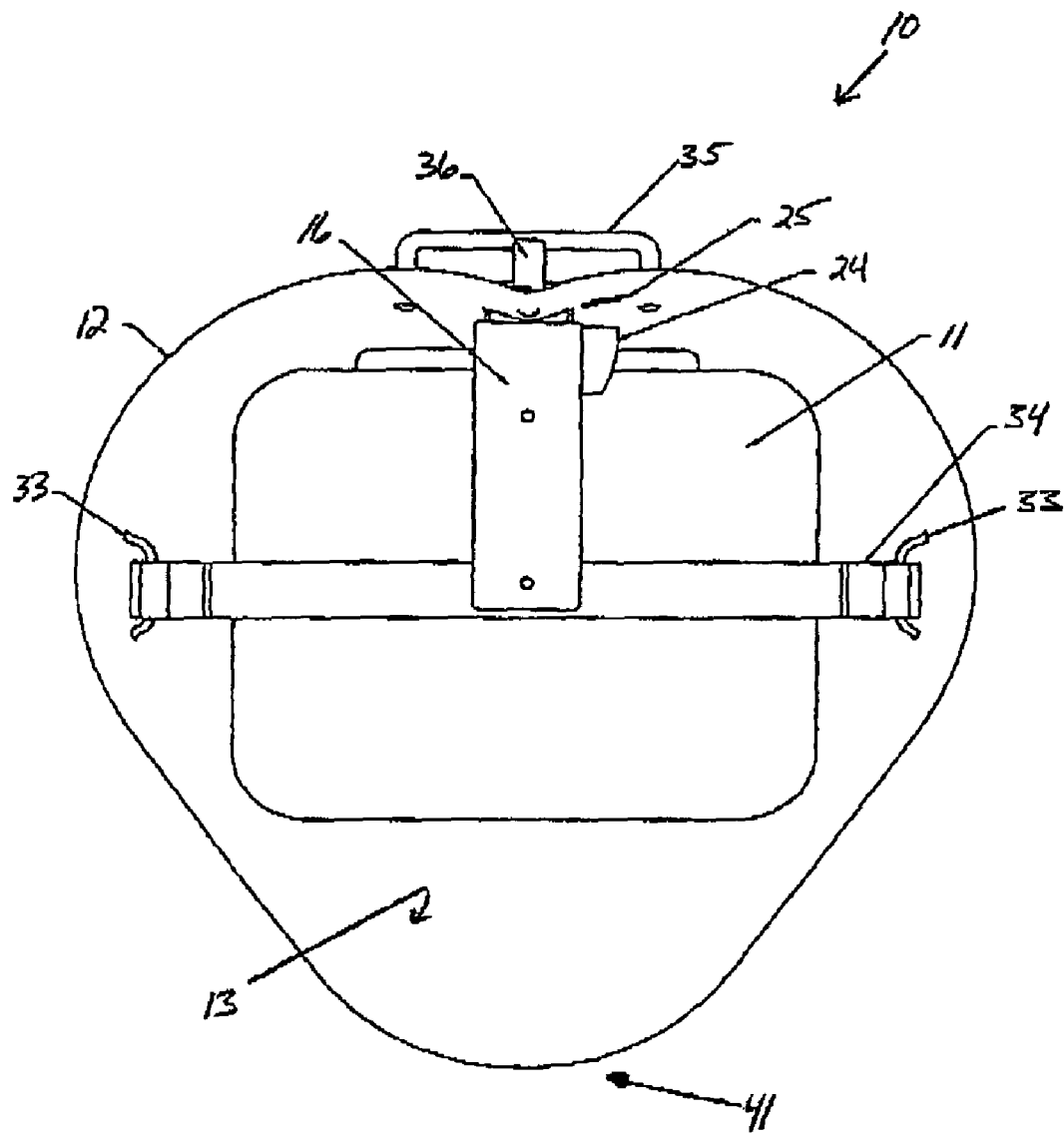
FIG. 6 is a posterior rear plan view of the first defibrillator storage assembly according to the present invention showing the wall mounting bracket, the defibrillator restraining strap, and a defibrillator restrained by said strap.

As generally depicted in FIG. 6, a relatively small alarm 24 may be mounted to the bracket 16 via hook and loop fastening means or similar other means. This alarm 24 is a self contained device of the type that may be used for remote window or door alarms. It is an audible alarm with a battery pack and a reed sensor. In the presence of the alarm magnet 25, the reed switch opens the circuit and the alarm 24 is off. Upon lifting the case or casing 12, pulling the magnet 25 attached to the casing 12 away from the alarm 24, the reed will close and the alarm 24 will sound. This could be reversed however, where the alarm 24 is attached to the casing 12, and the magnet 25 is attached to the bracket 16.

Figure 3:
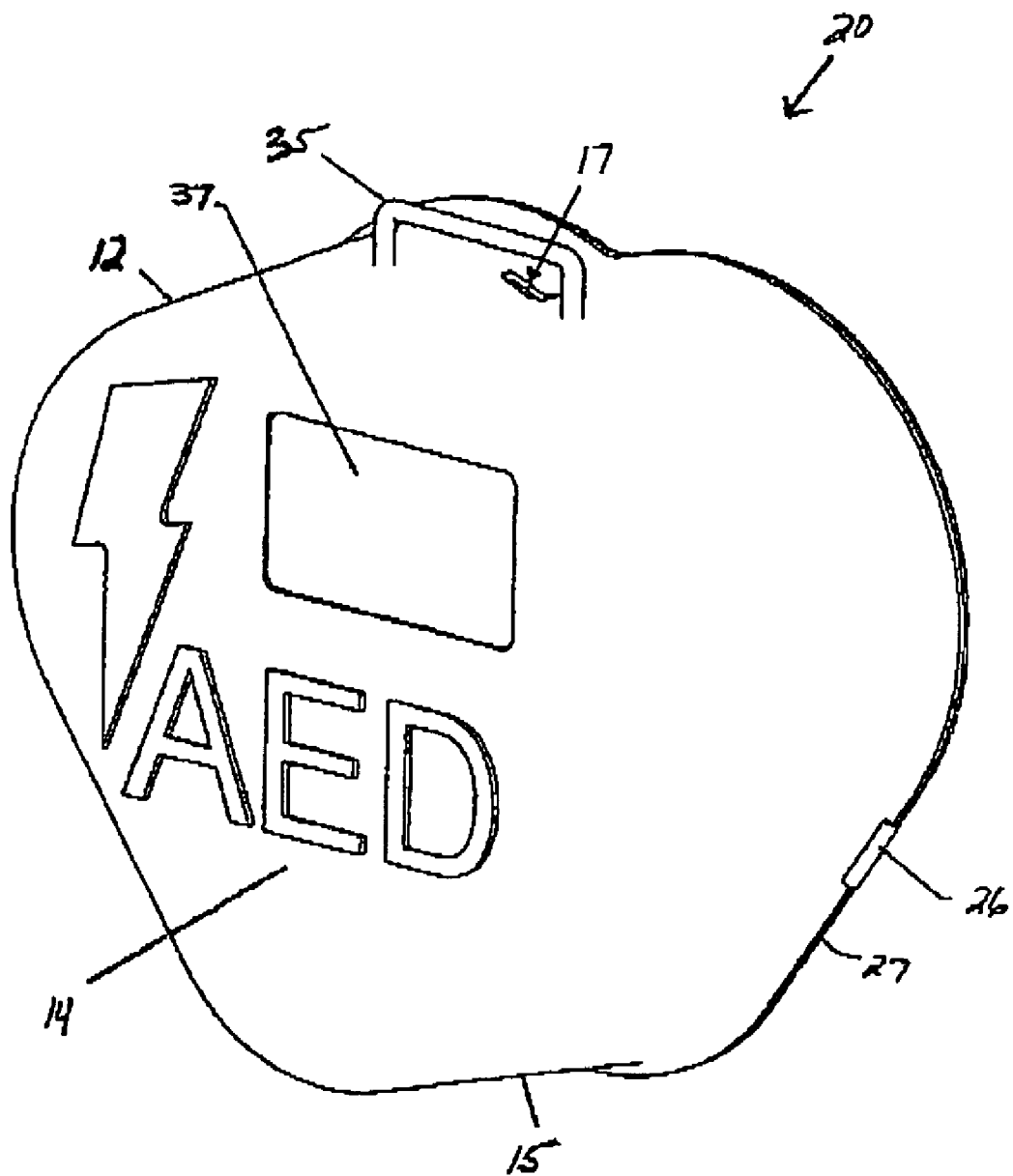
FIG. 3 is top front perspective type view of a second defibrillator storage assembly according to the present invention showing a mounting clip for restraining the outer assembly casing against an assembly support wall.
Figure 4:
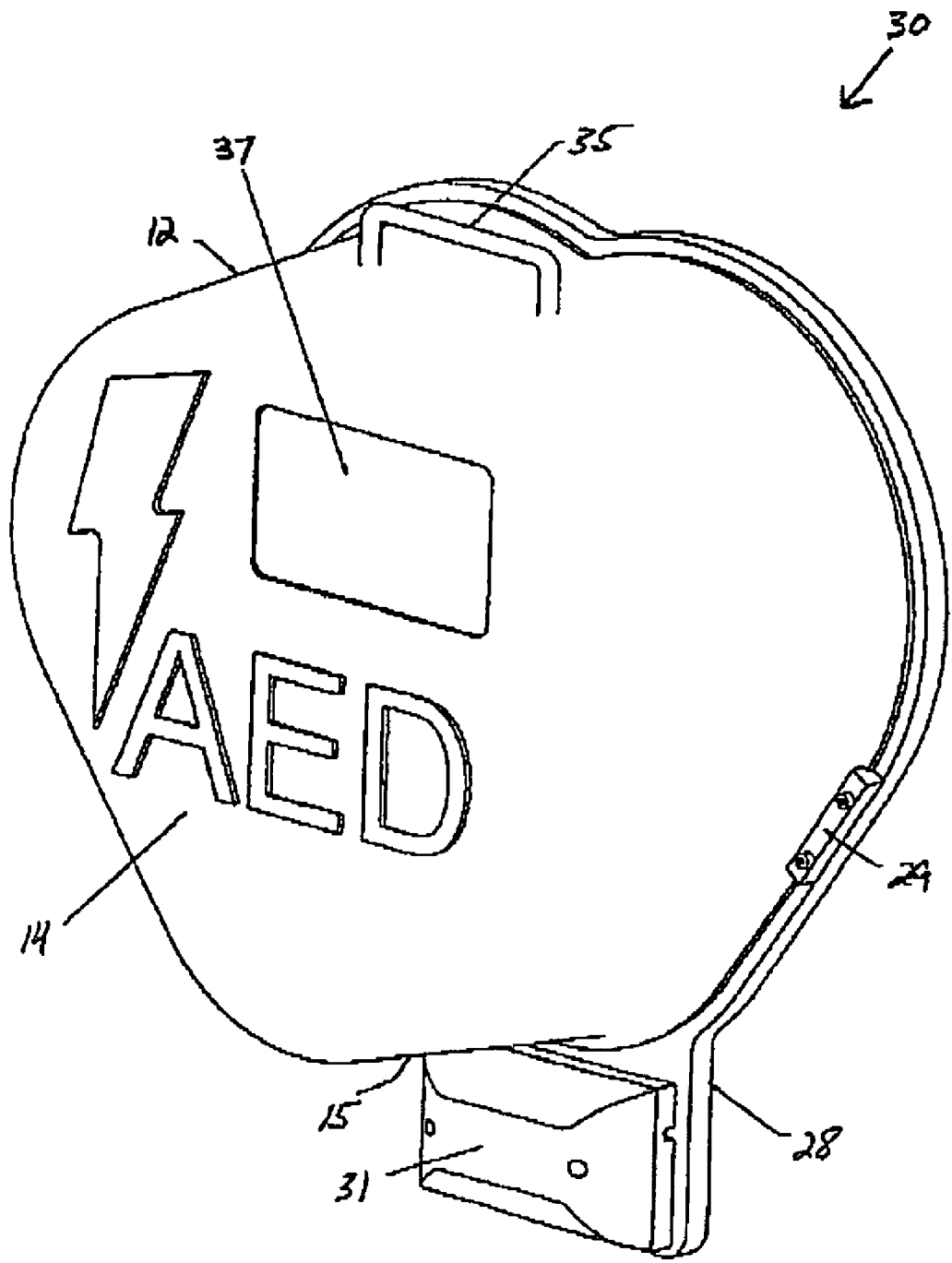
FIG. 4 is top front perspective type view of a third defibrillator storage assembly according to the present invention showing a back plate and mounting clip for restraining the outer assembly casing against an assembly support wall.
Figure 5:
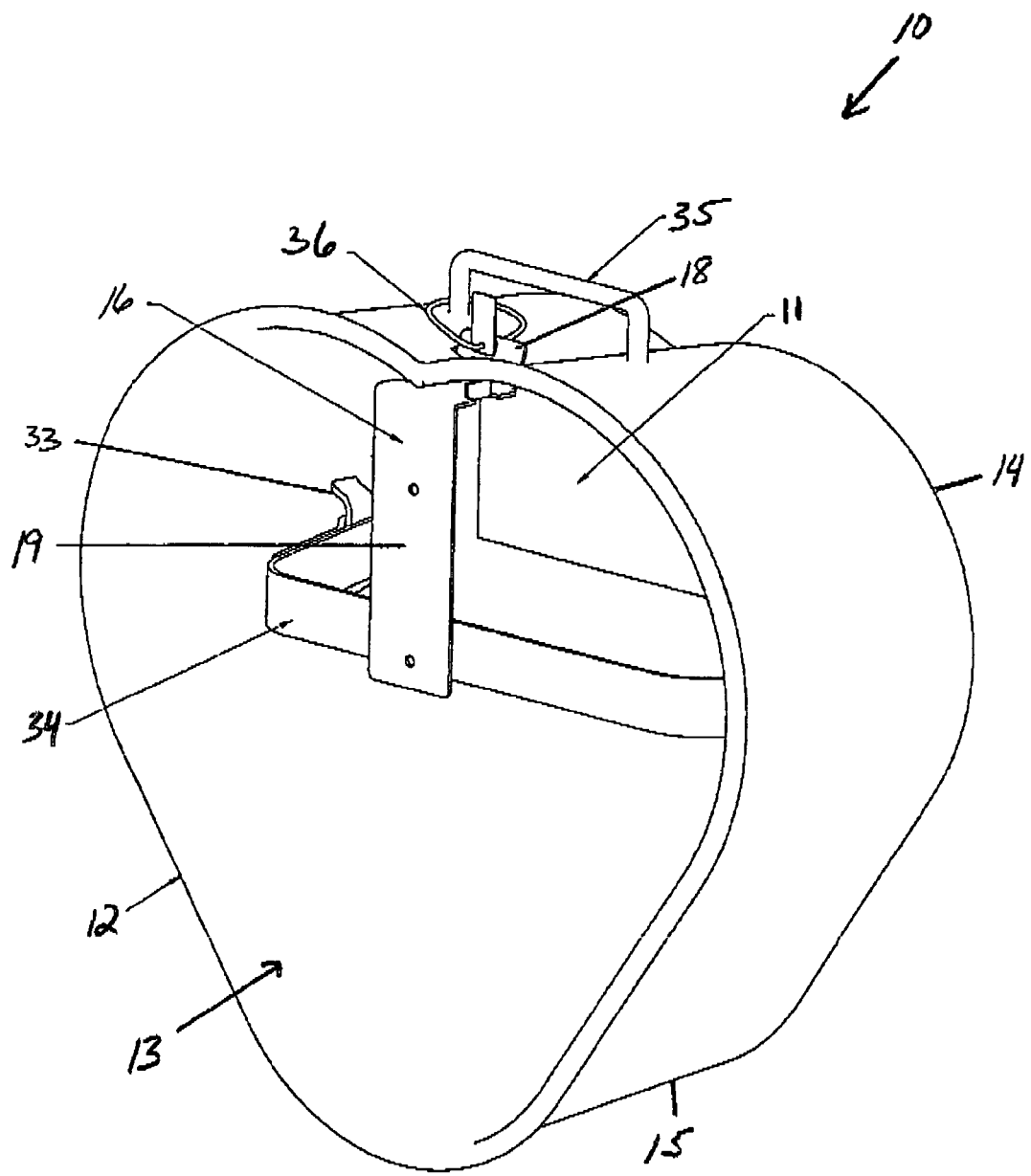
FIG. 5 is a posterior or rear perspective type view of the first defibrillator storage assembly according to the present invention showing a wall mounting bracket and a defibrillator restraining strap.

FIGS. 3 and 4 respectively depict alternative embodiments 20 and 30 of the defibrillator storage assembly according to the present invention. It is contemplated that embodiments 20 and 30 differ from embodiment or assembly 10 insofar as the cover mounting means are concerned. With regard to embodiment or assembly 20, said assembly 20 preferably comprises a back plate directly fastenable to an assembly support wall 22 (not specifically illustrated), which plate comprises clips 26 formed to engage the lower sloped portions 27 of the heart shape construction of the casing 12 as generally depicted in FIG. 3. Again, the alarm in this case is optional. In this situation the only difference from assembly 10 is that the audible alarm is mounted to the backing plate as opposed to the bracket 16.

Figure 9:
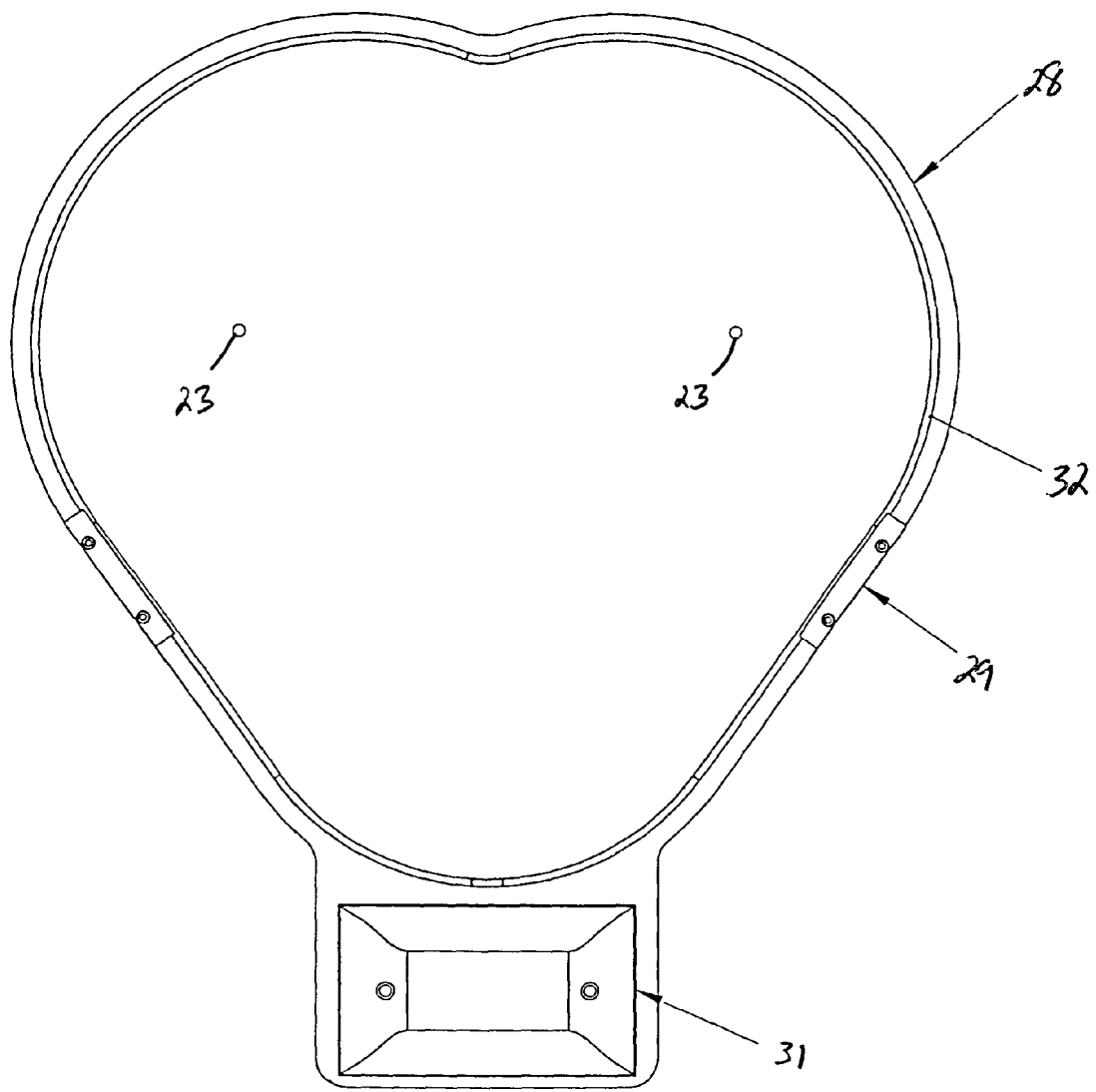
FIG. 9 is a front plan view of a wall mounting plate and exemplary alarm, which plate retains the outer assembly casing and which alarm alerts users to outer assembly casing removal from the wall mounting plate.

FIG. 4 is top front perspective type view of the third defibrillator storage assembly 30 showing a back or wall mounting plate 28 and mounting clips 29 for restraining the outer assembly casing 12 against the assembly support wall 22. FIG. 9 is a front plan view of the wall mounting plate 28 and exemplary alarm 29, which plate 28 retains the outer assembly casing 12 and which alarm 29 alerts users to removal of outer assembly casing 12 from the wall mounting plate 28.

In this case the audible alarm 31 is external to the cabinet or casing 12 and thus is also visible. The noted figures both show the alarm 31 below the casing 12; however the alarm 31 could conceivably be placed virtually anywhere relative to the casing 12. The alarm 31, for example, could conceivably be mounted up a pole for greater view from a long distance. In this case a reed switch or similar switch may operably sense a magnet within the casing 12. Upon removal, the absence of the magnet activates the alarm 31. It is contemplated that the reed switch and battery pack are embedded in the back plate 28 along with wires running to the alarm 31. An O-ring type seal or gasket 32 is further included to enhance the seal between the casing 12 and the back plate 28.

The defibrillator-restraining means for all embodiments or assemblies 10, 20, and 30 is believed well provided by a uniform construction as may be preferably defined by a strap 34 and certain strap connecting means, as may be further exemplified by pair of strap hooks 33. The defibrillator-restraining or defibrillator-retaining strap 34 removably restrains the defibrillator 11 as received within the cover structure or casing 12.

When the casing 12 is removed from any of the respectively described or exemplified cover mounting means, the strap 34 as end bound by the hooks 33, functions to retain the AED 11 within the casing 12 for transport to the user site. It is contemplated that in an alternative embodiment, the strap 34 could be eliminated such that the sloped sides 27 of the cover structure or casing 12 could function to support the AED 11 as received within the casing 12 (not specifically illustrated).

Figure 10:
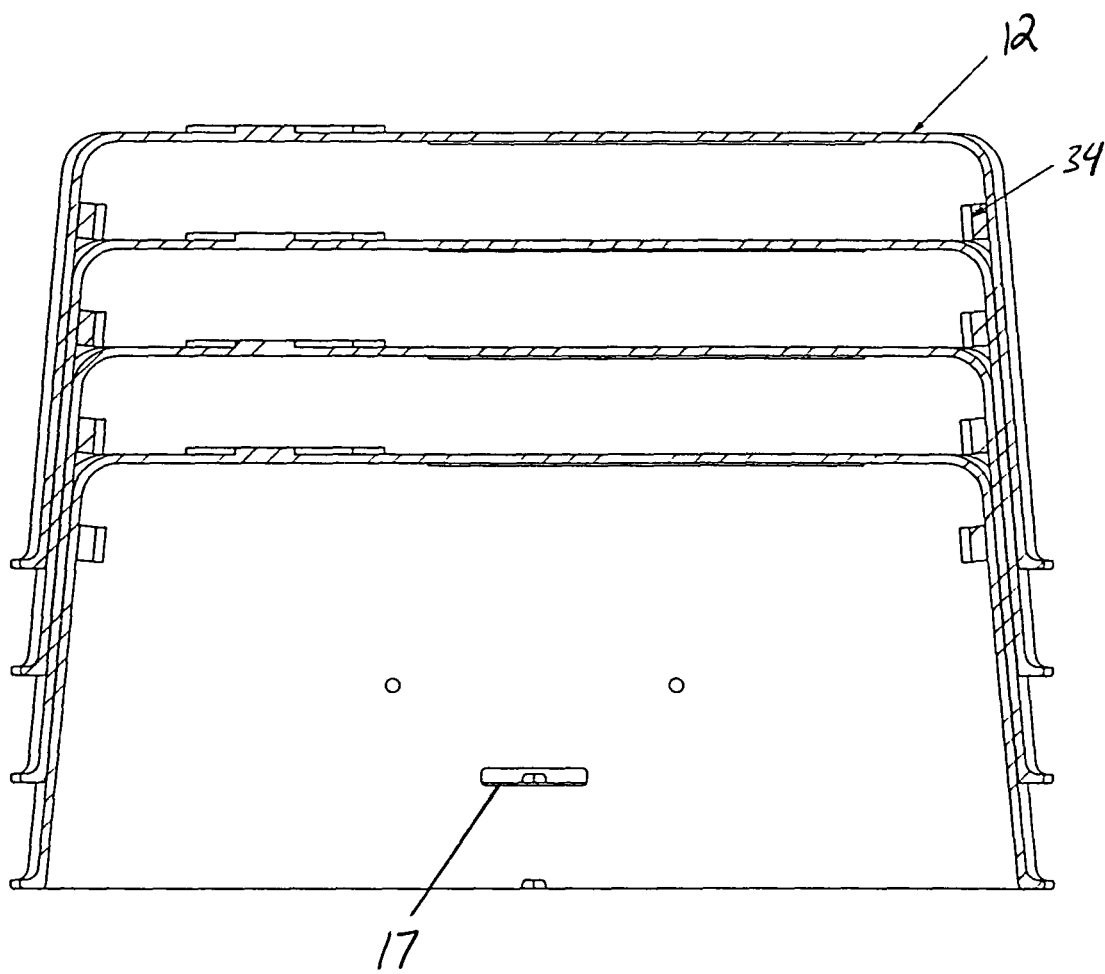
FIG. 10 is a cross-sectional side view of four outer assembly casings nested with one another, the defibrillator-restraining strap hooks providing nesting stop structures.

With the inside or internal components removed, the hooks 33 project inwardly to provide nesting stop structure as generally depicted in FIG. 10. In other words, to reduce the required space to store and/or transport multiple casings 12, the design allows the casing 12 to nest within one another. The hooks 33 provide nesting stop structure for easing the process of separating the casings 12 from an otherwise nested state.

For ease in identification, all of the devices or assemblies 10, 20, and 30 are preferably heart shaped and red from an anterior vantage point, although it is contemplated that color is less critical than shape. The preferred shape, from an anterior perspective, provides onlookers with an immediate visual prompt in response to a perceived emergency, which visual prompt and perceived emergency are linked by a common theme, namely heart and heart-related emergency.

To accommodate cost and portability goals, this assemblies 10, 20, and 30 are not wall mounted cases with a separate door formed in the front. Rather the assemblies 10, 20, and 30 each comprise an outer shell or casing 12 that house the defibrillator 11 and support equipment, has a handle 35 on the top for carrying the units, and which handle 35 may enable the user to mount the assemblies 10, 20, and/or 30 on a wall hook like an elaborate picture mount.

This picture mount or handle 35 may be outfitted with a breakable security tie 36 that may preferably attach to the case handle 35 and to the wall mounting bracket 16. Lifting the casing 12 by the handle 35 breaks the tie 36 and indicates that the casing 12 and AED 11 have been tampered with. As indicated, the bracket 16 may be outfitted with an optional alarm, such as alarm 24, such that removal of the AED 11 from the bracket 16/wall 22 will trigger the alarm 24.

It is contemplated that the casing 12 may be preferably injection molded or thermal formed to the heart shape and constructed of ASA plastic or similar. The plastic is ideal for corrosion resistance, low cost, and light weight. The casing 12 has a draft and is designed such that without the handle 35 the parts can be nested for compact, low cost transportation as generally illustrated in FIG. 10.

It is further contemplated that the front 14 of the casing 12 may preferably be outfitted with a lighting bolt and lettering that is of a different texture, all molded in for additional ease of identification. If desired the letters and bolt can be easily rolled a different color. The front 14 may further comprises a window 37, the size of which should be (1) minimized with a view toward limiting green house effects outdoors, and (2) maximized so as to position status indicators of the internal defibrillator 11 for easy identification externally.

On the interior of the casing 12, relatively close to the front 14 of the casing 12 on each lateral side of the casing 12 are the hooks 33 that are preferably molded in. These hooks 33 serve a dual purpose. Firstly, the hooks provide means for binding opposite ends of strap 34 (as may be exemplified by a strap outfitted with VELCRO brand hook and loop fastening means for ease of removable restraint) to hold the AED or defibrillator 11 in place during transport. Secondly, the hooks 33 may well function as certain means for controlling the nesting depth for transport such that the casings 12 do not otherwise lock together.

In most indoor applications the device will be used without a backing such as plate 28. The backing to the assembly could conceivably be provided by the wall 22. For outdoor or dirty applications, a backing plate 28 may be preferably provided. This plate 28 can also be heart shaped and has two slide rails or clips 29 that allow the casing to be slid into and tightly contained. The backing plate 28 may further comprise a seal as at 32 that is embedded into it such that at the final resting place of the casing 12. The sealing member 32 makes contact with the flat landing of the case flange. For these types of applications the window 37 may be preferably sealed into the casing 12 and the bracket slot 17 on top plugged or eliminated during the molding process.

While the above description contains much specificity, this specificity should not be construed as limitations on the scope of the invention, but rather as an exemplification of the invention. For example, it is contemplated that the present invention essentially provides a defibrillator-storage device combination for enabling would-be users to quickly identify defibrillator location and carry a defibrillator to a user site. The combination may be said to comprise a defibrillator, a cover structure or casing, certain cover mounting means, and certain defibrillator-restraining means. The cover structure comprises an open back, a closed front, a wall extending from the front to the back, and a heart-shaped transverse cross-section.

The wall spaces the front from the back and has a transverse periphery sufficient to receive the defibrillator. The cover mounting means essentially function to mount the cover structure to a wall, and are thus attachable to both the support wall and the cover structure. The defibrillator-restraining means essentially function to removably restrain the defibrillator as received within the cover structure either for storage or for transport purposes.

The cover structure may comprise a window for enabling a user to view inside the cover structure to visually inspect a(n automatic external) defibrillator as otherwise covered or housed by the cover structure. The wall may comprise an upper dipped portion and a lower pointed portion, which upper dipped may preferably comprise a handle for enabling a user to carry the cover structure and defibrillator to a user site, which defibrillator is restrained by the defibrillator-restraining means.

Further, it is contemplated that the cover structure or casing 12 could be outfitted with a (snapping) back or backing akin to a sealing lid, both for holding in the AED as well as sealing the space defined by the cover structure and the contemplated backing from moisture. Alternatively, the otherwise open back as at 13 could conceivably be outfitted with a flexible backing such as a nylon fabric that would attached to the wall 15 and may even have pouches for storage of items (not specifically illustrated).

The cover mounting means may be variously defined. For example, the cover mounting means may be defined by a back plate having a heart-shaped portion and being attachable to a wall, said back plate comprising means for removably attaching the cover structure to the heart-shaped portion such as clips 29 or 26. Alternatively, the cover mounting means may be defined by a bracket assembly cooperable with the dipped top portion having a slot. The bracket assembly may comprise a wall mounting portion such as portion 19 and an upwardly extending protrusion as at 18. The protrusion 18 is receivable by the slot as at 17 and the bracket assembly (as at structure 21) thus functions to support the dipped upper portion upon the bracket 16.

The cover structure or casing 12 may be nested with at least one additional cover structure or casing 12 for reducing the space necessary for storage and/or transport of the cover structures. The defibrillator-restraining means may preferably comprise strap connecting means (such as hooks 33), which strap connecting means extend inwardly relative to the wall for providing certain nest stop structure for the nestable cover structures. All assemblies may be optionally outfitted with certain alarm means substantially as described herein.

Accordingly, although the invention has been described by reference to certain preferred and alternative embodiments, it is not intended that the novel disclosures herein presented be limited thereby, but that modifications thereof are intended to be included as falling within the broad scope and spirit of the foregoing disclosure, the following claims and the appended drawings.

We claim:

1. A defibrillator-storage and transport assembly for storing and transporting an assembly-stored defibrillator, the assembly comprising:

a unitary cover structure, the cover structure comprising an open. back, a closed front, a closed wall extending from the closed front to the open back, and a heart-shaped transverse cross-section, the open back thus having a heart-shaped back periphery and the closed front thus having a heart-shaped front periphery for providing a defibrillator-related, heart-themed visual, the closed wall spacing the closed front from the open back and having a transverse heart-shaped wall periphery sufficient to receive a defibrillator, an assembly-received defibrillator being only accessible via the open back;

defibrillator-restraining means for removably restraining an assembly-received defibrillator as received within the cover structure; and a back plate for removably mounting the cover structure to a support wall, the back plate comprising a heart-shaped portion and being attachable to the support wall and removably attachable to the cover structure, said back plate comprising means for removably attaching the cover structure to the heart-shaped portion, the support wall closing the open back when the cover structure is mounted to the support wall via the back plate, an assembly-restrained defibrillator, the defibrillator-restraining means and cover structure together being simultaneously and selectively removable from the support wall via the back plate, and together being simultaneously transportable to a user site.

2. The assembly of claim 1 wherein the closed front comprises a translucent window, the translucent window for enabling a user to view a defibrillator portion as housed within the cover structure, the closed front having a total surface area, the total surface area comprising a maximized opaque portion for enhancing the defibrillator-related, heart-themed visual, the window being minimized for maximizing the opaque portion.

3. The assembly of claim 1 wherein the cover structure comprises a handle for enhancing a user's ability to manually grab and transport the cover structure with defibrillator-restraining means and an assembly-restrained defibrillator as received therein.

4. The assembly of claim 1 wherein the closed wall enables a user to nest a series of identical cover structures, the cover structure thus being instable with at least one additional cover structure.

5. The assembly of claim 4 wherein the defibrillator-.restraining means comprise strap-connecting means, the strap-connecting means extending inwardly relative to the closed wall substantially parallel to the closed front, the strap-connecting means thereby providing nest stop structure for the nestable cover structures.

6. The assembly of claim 1 comprising alarm means for providing an alarm when the cover structure with defibrillator-restraining means and the assembly-restrained defibrillator is removed from the cover-mounting means.

7. A defibrillator-storage and transport assembly for storing and transporting an assembly-stored defibrillator, the assembly comprising:

a unitary cover structure, the cover structure comprising an open back, a closed front, a closed wall extending from the closed front to the open back, and a heart-shaped transverse cross-section, the open back thus having a heart-shaped back periphery and the closed front thus having a heart-shaped front periphery for providing a defibrillator-related, heart-themed visual, the closed wall comprising an aperture and spacing the closed front from the open back and having a transverse heart-shaped wall periphery sufficient to receive a defibrillator, an assembly-received defibrillator being only accessible via the open back;

defibrillator-restraining means for removably restraining an assembly-received defibrillator as received within the cover structure; and a bracket assembly for removably mounting the cover structure to a support wall, the bracket assembly being attachable to the support wall and removably attachable to the cover structure, the bracket assembly comprising a wall-mounting portion and an aperture-penetrating portion, the aperture-penetrating portion being receivable by the aperture for supporting the cover structure upon the bracket assembly, the support wall closing the open back when the cover structure is mounted to the support wall via the bracket assembly, an assembly-restrained defibrillator, the defibrillator-restraining means and cover structure together being simultaneously and selectively removable from the support wall via the bracket assembly, and together being simultaneously transportable to a user site.

8. The assembly of claim 7 wherein the closed front comprises a translucent window, the translucent window for enabling a user to view a defibrillator portion as housed within the cover structure, the closed front having a total surface area, the total surface area comprising a maximized opaque portion for enhancing the defibrillator-related, heart-themed visual, the window being minimized for maximizing the opaque portion.

9. The assembly of claim 7 wherein the cover structure comprises a handle for enhancing a user's ability to manually grab and transport the cover structure with defibrillator-restraining means and an assembly-restrained defibrillator as received therein.

10. The assembly of claim 7 wherein the closed wall enables a user to nest a series of identical cover structures, the cover structure thus being mestable with at least one additional cover structure.

11. The assembly of claim 10 wherein the defibrillator-restraining means comprise strap-connecting means, the strap-connecting means extending inwardly relative to the closed wall substantially parallel to the closed front, the strap-connecting means thereby providing nest stop structure for the nestable cover structures.

12. The assembly of claim 7 comprising alarm means for providing an alarm when the cover structure with defibrillator-restraining means and The assembly-restrained defibrillator is removed from the cover-mounting means.

13. A defibrillator-storage and transport assembly for storing and transporting an assembly-stored defibrillator, the assembly comprising:

a unitary cover structure, the cover structure comprising an open back, a closed front, a closed wall extending from the closed front to the open back, and a heart-shaped transverse cross-section, the open back thus having a heart-shaped back periphery and the closed front thus having a heart-shaped front periphery for providing a defibrillator-related, heart-themed visual, the closed wall spacing the closed front from the open back and having a transverse heart-shaped wall periphery sufficient to receive a defibrillator, an assembly-received defibrillator being only accessible via the open back;

defibrillator-restraining means for removably restraining au assembly-received defibrillator as received within the cover structure; and a bracket assembly for removably mounting the cover structure to a support wall, the bracket assembly being attachable to the support wall and removably engageable with the cover structure, the bracket assembly comprising a wall-mounting portion and a cover structure support portion, the cover structure support portion being engageable with the cover structure for supporting the cover structure upon the bracket assembly, the support wall closing the open back when the cover structure is mounted to the support wall via the bracket assembly, an assembly-restrained defibrillator, the defibrillator-restraining means and cover structure together being simultaneously and selectively removable from the support wall via the bracket assembly, and together being simultaneously transportable to a user site.

* * * * *